(12) United States Patent
Cameron et al.

(10) Patent No.: US 7,827,993 B2
(45) Date of Patent: Nov. 9, 2010

(54) SKIN PRESSURE REDUCTION TO PREVENT DECUBITUS ULCERS BY PARTIAL MAGNETIC LEVITATION

(75) Inventors: Graham P. Cameron, Rochester, MN (US); Wayne H. Fjerstad, Rochester, MN (US); Barry K. Gilbert, Rochester, MN (US); Kenton R. Kaufman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 294 days.

(21) Appl. No.: 11/997,175

(22) PCT Filed: Jul. 28, 2006

(86) PCT No.: PCT/US2006/029681
§ 371 (c)(1),
(2), (4) Date: Jan. 29, 2008

(87) PCT Pub. No.: WO2007/016460
PCT Pub. Date: Feb. 8, 2007

(65) Prior Publication Data
US 2008/0281144 A1 Nov. 13, 2008

Related U.S. Application Data

(60) Provisional application No. 60/703,743, filed on Jul. 29, 2005.

(51) Int. Cl.
*A61B 19/00* (2006.01)
(52) U.S. Cl. .................................................... 128/899
(58) Field of Classification Search ................ 335/219; 600/9–15; 297/284.3; 128/899
See application file for complete search history.

(56) References Cited

U.S. PATENT DOCUMENTS

| | | | |
|---|---|---|---|
| 3,670,725 A | 6/1972 | Gaylord, Jr. | |
| 4,382,245 A | 5/1983 | Harrigan | |
| 5,054,142 A | 10/1991 | Owens | |
| 5,243,723 A | 9/1993 | Cotner et al. | |
| 5,473,313 A | 12/1995 | Graebe, Jr. | |
| 5,507,835 A | 4/1996 | Jore | |
| 5,529,568 A | 6/1996 | Rayman | |
| 5,876,364 A | 3/1999 | Herbst | |
| 6,231,496 B1 * | 5/2001 | Wilk et al. | 600/9 |
| 6,349,439 B1 | 2/2002 | Cook et al. | |
| 6,367,106 B1 | 4/2002 | Grons | |
| 6,379,295 B1 * | 4/2002 | Woo | 600/15 |
| 6,413,138 B1 | 7/2002 | Dokoupil | |
| 6,895,973 B2 * | 5/2005 | Lewallen | 128/899 |

OTHER PUBLICATIONS

International Search Report and Written Opinion corresponding to PCT/US2006/029681 under date of mailing of Jan. 26, 2007.

* cited by examiner

*Primary Examiner*—Samuel G Gilbert
(74) *Attorney, Agent, or Firm*—Quarles & Brady, LLP

(57) ABSTRACT

A magnetic levitation system for immobile patients in a wheelchair is disclosed. A magnet multi-pole configuration that is mechanically stable is provided that lifts the body and/or load shifts (rotates the body from side to side) the body. Based on a multi-pole configuration of permanent magnets in the pelvis, a corresponding multi-pole configuration for magnet repulsion is placed below the patient, typically as part of the wheelchair. Alternatively, a unipolar repulsion with mechanical patient restraint is implemented to achieve body lift or levitation. Either permanent magnets or electromagnets, optionally with magnetic sensor-mediated active computerized feedback control below the body, are sufficient to implement a complete multi-pole repulsive configuration that is mechanically stable. The apparatus reduces compressive force on soft tissues disposed between a human pelvis and a wheelchair seat.

30 Claims, 10 Drawing Sheets

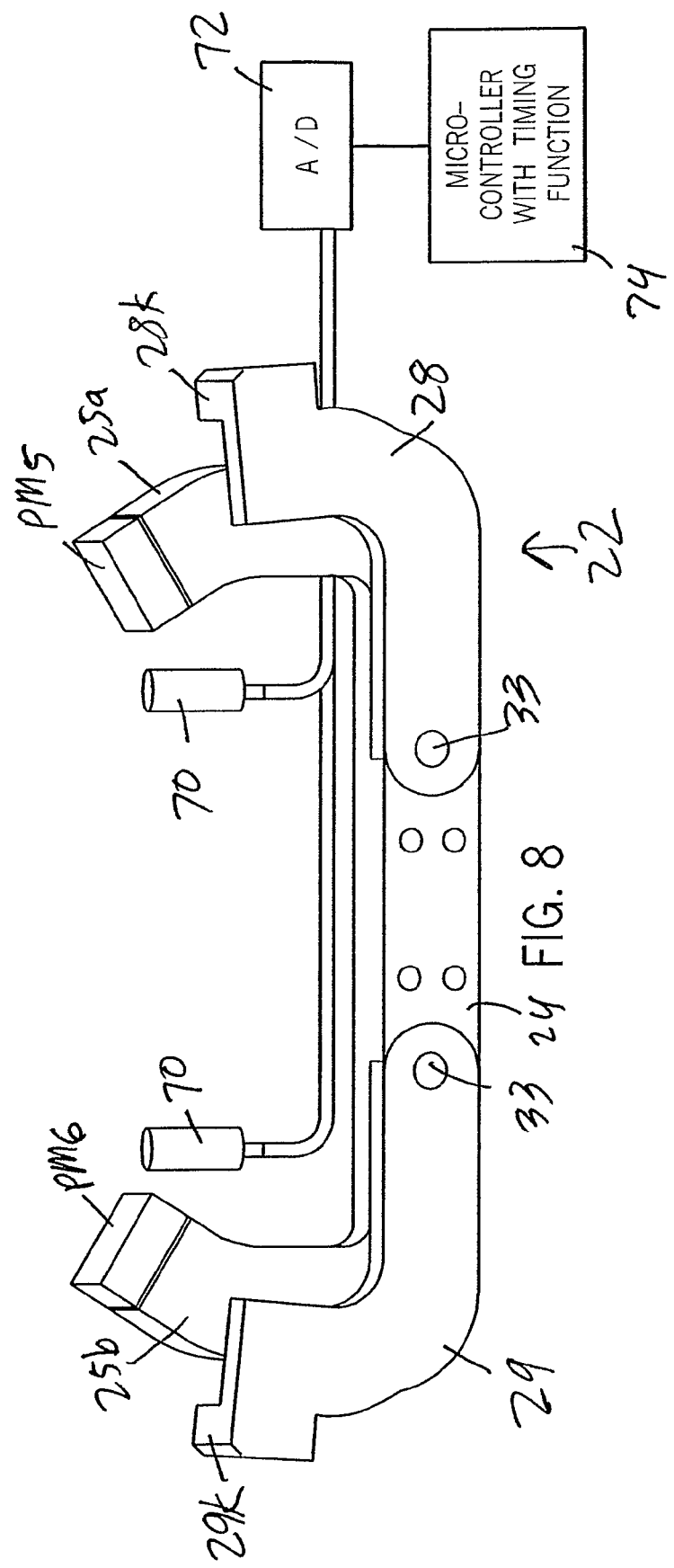

SKIN PRESSURE REDUCTION TO PREVENT DECUBITUS ULCERS BY PARTIAL MAGNETIC LEVITATION

CROSS-REFERENCES TO RELATED APPLICATIONS

This application claims priority from U.S. Provisional Patent Application No. 60/703,743 filed Jul. 29, 2005.

STATEMENT REGARDING FEDERALLY SPONSORED RESEARCH

Not Applicable.

BACKGROUND OF THE INVENTION

1. Field of the Invention

This invention relates to an apparatus and method for reducing compressive forces on soft tissue disposed between a bone, such as a human pelvis, and a supporting structure, such as the seat of a wheel chair.

2. Description of the Related Art

Many immobile (i.e. paraplegic, quadriplegic, cerebral palsy) patients are seated in a wheelchair during all or most of their waking hours. Open skin wounds or sores (decubitus ulcers) form on the buttocks of the patient due to a lack of blood flow in the skin from the constant pressure of their own weight. The ischial tuberosity is the most common site for pressure sores, accounting for 28% of all ulcers. Pressure sores are a significant and common cause of morbidity and mortality in spinal cord injury patients. Considering the gradual decline in mortality rates from spinal cord injuries, coupled with an aging population, it is conceivable that the group of patients prone to developing pressure sores will increase in the future. The bulk of the literature to date has primarily focused on the technical aspects of surgical management of pressure sores.

It is well established that the principle, and often solitary, cause of the decubital ulcers is excessive pressure, usually on a bony prominence in susceptible individuals. Sitting posture naturally creates high contact pressures at both ischial tuberosities, the coccyx, and in some cases the greater trochanters. The magnitude of contact pressure over ischial tuberosities has been found to correlate well with incidence of pressure sores. As a result of immobility and impaired protective sensation, wheelchair-bound spinal cord injury patients are at ongoing significant risk of pressure sores in these regions.

The needs of immobile patients in a wheelchair and their caregivers vary widely. The physical functionality of spinal cord injury patients has wide variation based on the position of the injury along the spinal cord. Patients with cerebral palsy and other degenerative diseases each have their own set of wheelchair requirements. Another important consideration is that most people confined to a wheelchair commonly have chronic shoulder and elbow injuries. Caregivers also suffer from chronic problems. Transferring patients in and out of a wheelchair and the weight of the wheelchair itself contribute to these chronic problems. As blood flow in the skin under compression below the lower pelvis in patients confined to wheelchairs becomes better understood, the needs of patients and caregivers will be further delineated.

Skin pressure can be reduced by partial levitation of the patient using repulsive forces generated by magnets. Permanent magnets may be surgically implanted in the patient's lower pelvis (ischium) and magnets below the seat or at the seat surface of a wheelchair repel the magnets surgically implanted in the lower pelvis. The purpose of these magnets is to partially lift the patient. Partial levitation of the patient allows blood to flow in the patient's skin, thereby reducing the tendency for decubitus ulceration. See, for example, U.S. Pat. No. 6,895,973 and corresponding U.S. Patent Application Publication No. 2004/0077922.

However, there is still a need for an improved magnetic levitation system that provides for enhanced lift and load shift capabilities for immobile patients in a wheelchair.

SUMMARY OF THE INVENTION

The present invention meets the foregoing needs by providing an improved magnetic levitation system for immobile patients in a wheelchair. A magnet multi-pole configuration that is mechanically stable is provided that lifts the body and/or load shifts (rotates the body from side to side) the body. Based on a multi-pole configuration of permanent magnets in the pelvis, a corresponding multi-pole configuration for magnet repulsion is placed below the patient, typically as part of the wheelchair. Alternatively, a unipolar repulsion with mechanical patient restraint is implemented to achieve body lift or levitation. Either permanent magnets or electromagnets, optionally with magnetic sensor-mediated active computerized feedback control below the body, are sufficient to implement a complete multi-pole repulsive configuration that is mechanically stable. Parts or the total permanent magnet or electromagnets embodiment can be applied, depending on patient and caregiver needs.

In one aspect, the invention provides an apparatus for reducing compressive forces on soft tissue disposed between a bone in a subject and a supporting structure. The apparatus includes a first bone magnet suitable for implantation into the bone, a second bone magnet suitable for implantation into the bone, a first support structure magnet attached to a base positioned adjacent the supporting structure, a second support structure magnet attached to the base, and means for moving the base with respect to the supporting structure. The first support structure magnet and the second support structure magnet are typically positioned below the supporting structure. The first bone magnet and the first support structure magnet are positioned such that a repelling force is produced that acts on the first bone magnet and the first support structure magnet to reduce the compressive force acting on the soft tissues disposed therebetween, and the second bone magnet and the second support structure magnet are arranged such that a repelling force is produced that acts on the second bone magnet and the second support structure magnet to reduce the compressive force acting on the soft tissues disposed therebetween.

The means for moving the base can be means for rotating the base about an axis of the base such that the first bone magnet can move away or toward the first support structure magnet and such that the second bone magnet can move away or toward the second support structure magnet. The means for moving the base can also be means for translating the base such that the first bone magnet can move away or toward the first support structure magnet and such that the second bone magnet can move away or toward the second support structure magnet. Preferably, the first support structure magnet and the second support structure magnet are spaced apart on opposite sides of an axis of the base. Typically, the supporting structure is a seat of a wheelchair, and the bone is a human pelvis. The wheelchair may include a mechanical restraint for the person.

In one form, the apparatus includes a third bone magnet suitable for implantation into the bone, a fourth bone magnet suitable for implantation into the bone, a third support structure magnet attached to the base, and a fourth support structure magnet attached to the base. The third bone magnet and the third support structure magnet are positioned such that a repelling force is produced that acts on the third bone magnet and the third support structure magnet to reduce the compressive force acting on the soft tissues disposed therebetween, and the fourth bone magnet and the fourth support structure magnet are arranged such that a repelling force is produced that acts on the fourth bone magnet and the fourth support structure magnet to reduce the compressive force acting on the soft tissues disposed therebetween. The first support structure magnet and the second support structure magnet may be positioned in spaced relationship on a side of an axis of the base, and the third support structure magnet and the fourth support structure magnet may be positioned in spaced relationship on an opposite side of the axis of the base. Optionally, the first support structure magnet has a larger pole piece than the second support structure magnet, and the third support structure magnet has a larger pole piece than the fourth support structure such that the magnets anteriorly arranged on the wheelchair and pelvis have larger pole pieces. The bone magnets and the support structure magnets may be electromagnets and/or permanent magnets. The apparatus may include means for increasing and decreasing magnetic flux flow in the first support structure magnet and the second support structure magnet such that patient shifting can be achieved in the wheelchair.

In another aspect, the invention provides an apparatus for reducing compressive forces on soft tissue disposed between a bone in a subject and a supporting structure. The apparatus includes a first bone magnet suitable for implantation into the bone, a second bone magnet suitable for implantation into the bone, a first support structure magnet positioned adjacent the supporting structure, a second support structure magnet positioned adjacent the supporting structure. The first support structure magnet and the second support structure magnet are typically positioned below the supporting structure. The first bone magnet and the first support structure magnet are positioned such that a first repelling force from north-north magnetic repulsion is produced that acts on the first bone magnet and the first support structure magnet to reduce the compressive force acting on the soft tissues disposed therebetween, and the second bone magnet and the second support structure magnet are arranged such that a second repelling force from south-south magnetic repulsion is produced that acts on the second bone magnet and the second support structure magnet to reduce the compressive force acting on the soft tissues disposed therebetween.

The apparatus may include means for moving the base with respect to the supporting structure. The means for moving the base may be means for rotating the base about an axis of the base such that the first bone magnet can move away or toward the first support structure magnet and such that the second bone magnet can move away or toward the second support structure magnet. The means for moving the base may be means for translating the base such that the first bone magnet can move away or toward the first support structure magnet and such that the second bone magnet can move away or toward the second support structure magnet.

The apparatus may include a third bone magnet suitable for implantation into the bone, a fourth bone magnet suitable for implantation into the bone, a third support structure magnet positioned adjacent the supporting structure, and a fourth support structure magnet positioned adjacent the supporting structure. The third bone magnet and the third support structure magnet are positioned such that a third repelling force from north-north magnetic repulsion is produced that acts on the third bone magnet and the third support structure magnet to reduce the compressive force acting on the soft tissues disposed therebetween, and the fourth bone magnet and the fourth support structure magnet are arranged such that a fourth repelling force from south-south magnetic repulsion is produced that acts on the fourth bone magnet and the fourth support structure magnet to reduce the compressive force acting on the soft tissues disposed therebetween. The first support structure magnet and the second support structure magnet may be positioned in spaced relationship on a side of an axis of a base, and the third support structure magnet and the fourth support structure magnet may be positioned in spaced relationship on an opposite side of the axis of the base. The bone magnets may be electromagnets and/or permanent magnets.

The apparatus may include means for increasing and decreasing magnetic flux flow in the first, second, third and/or fourth support structure magnets. The apparatus may further include means for sensing alignment of the first bone magnet and the first support structure magnet, and/or the second bone magnet and the second support structure magnet, and/or the third bone magnet and the third support structure magnet, and/or the fourth bone magnet and the fourth support structure magnet.

In yet another aspect, the invention provides a method for reducing compressive force on soft tissues disposed between a bone and a supporting structure. In the method, a first bone magnet is implanted in the bone, a second bone magnet is implanted in the bone, a first support structure magnet is positioned adjacent to the supporting structure, and a second support structure magnet is positioned adjacent to the supporting structure. The first support structure magnet and the second support structure magnet are typically positioned below the supporting structure. The first bone magnet and the first support structure magnet are positioned such that a first repelling force from north-north magnetic repulsion is produced that acts on the first bone magnet and the first support structure magnet to reduce the compressive force acting on the soft tissues disposed therebetween. The second bone magnet and the second support structure magnet are arranged such that a second repelling force from south-south magnetic repulsion is produced that acts on the second bone magnet and the second support structure magnet to reduce the compressive force acting on the soft tissues disposed therebetween.

In the method, the first bone magnet may be moved away or toward the first support structure magnet, and/or the second bone magnet may be moved away or toward the second support structure magnet. The magnetic flux flow in the first support structure magnet and/or the second support structure magnet may be increased or decreased. In one example, the bone is the ischial tuberosity of the pelvis of a human seated in a wheelchair and the supporting structure is a seat of the wheelchair.

Thus, it is an advantage of the present invention to provide an apparatus for reducing compressive forces on soft tissue disposed between a bone in a subject and a supporting structure.

It is another advantage to provide a method for reducing compressive force on soft tissues disposed between a bone and a supporting structure.

These and other features, aspects, and advantages of the present invention will become better understood upon consideration of the following detailed description, drawings and appended claims.

BRIEF DESCRIPTION OF THE DRAWINGS

FIG. 3 shows the magnetic flux repulsion pattern with body magnets and magnets positioned below a wheel chair seat.

FIG. 8 shows a perspective view of the magnetic assembly of FIG. 5 in a maximum lift position.

Like reference numerals will be used to refer to like or similar parts from Figure to Figure in the following description of the invention.

DETAILED DESCRIPTION OF THE INVENTION

Figure 1:
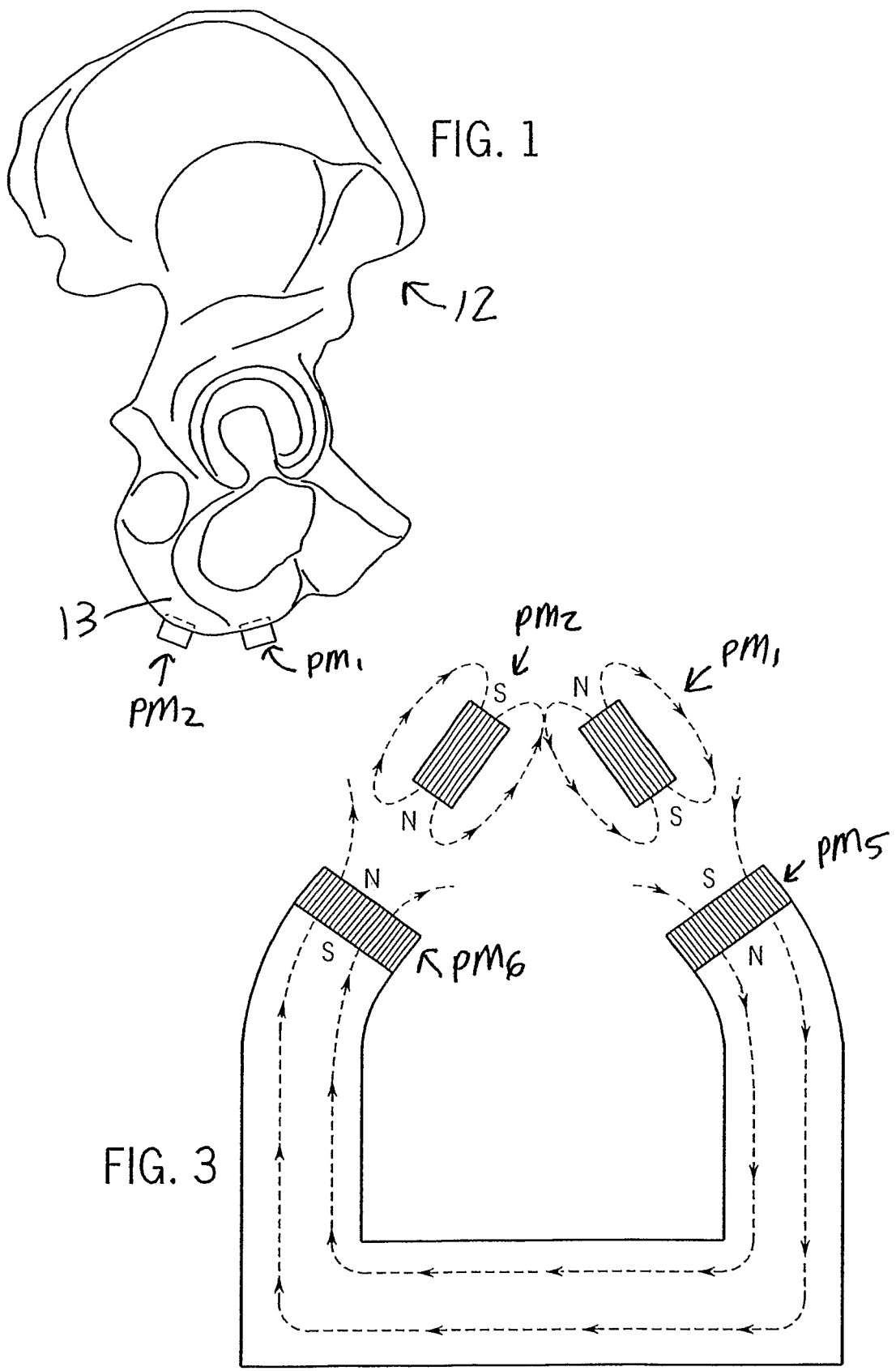
FIG. 1 is a right side view of a human pelvis having implanted magnets.

The invention disclosed herein instructs on how to reduce the pressure on the buttocks, thereby preventing sores by allowing sufficient oxygenated blood flow to the skin and underlying soft tissues. Skin pressure can be reduced by partial levitation of the patient using repulsive forces generated by magnets. Permanent magnets may be surgically implanted in the patient's lower pelvis (ischium), and magnets below the seat or at the seat surface of a wheelchair can be configured to repel the magnets surgically implanted in the lower pelvis. The purpose of these magnets is to partially lift the patient or load shift the patient's weight from side to side. Partial levitation of the patient allows blood to flow in the patient's skin, thereby reducing the tendency for decubitus ulceration.

Operational requirements of wheelchair patients and their caregivers not only include lift and load shift, but also include transfer into and out of the wheelchair and recharging of the permanent magnets. The emphasis on each of these operational requirements can vary widely due to patient's daily living and physical conditions. Partial or full levitation can create lift off the seat of a wheelchair. In effect, lift creates a magnetic cushion. Lift requires a net vertical force upward. Forces for both side-to-side stability and anterior-to-posterior stability are lateral forces that must be equal and opposite with no net horizontal force. Applying more lift to one side of the body than to the other side of the body shifts the weight bearing load of the patient's body weight from one side to the other side. Load shift can be accomplished by increasing the spacing between magnets (reducing magnetic force) on one side of the body and decreasing magnet spacing (increasing magnetic force) on the other side of the body. Load shift can also be implemented by applying a mechanical lift to one side of the body and not to the other, or by augmenting the field strength on one side of the body using auxiliary electromagnets that may be computer-controlled.

Patient transfer into and out of a wheelchair has operational requirements complicated by unpredictable body shift during the transfer along with the multipole magnetic system described below. Transfer into the wheelchair requires alignment of the body magnets with magnets below the seat before repulsive magnetic forces are applied to the body. The magnet forces below the seat must be turned off before the patient enters the wheelchair in order to avoid unintentional loading. Alignment of the body to the proper magnetic poles is sensed by a magnetic field sensor and connected to the usual electronic configuration of an analog-to-digital converter that is input to a digital micro-controller. The micro-controller then provides positional feedback to humans or a mechanical compensation system for the body position. Once the patient is found to be in the proper position, repulsive magnet forces can be applied to the permanent magnets in the body. Transfer out of the wheelchair has the requirement that the magnetic lifting force be turned off if the patient unexpectedly returns back into the wheelchair. One way to accomplish transfer out of the wheelchair is to simply turn off the magnetic forces below the wheelchair before the patient begins to transfer out of the wheelchair. Another way is to boost the forces to the assist the transfer process. Then, to prevent accidents if the patient falls back into the wheelchair, magnets below the chair must be turned off as the patient rises out of the seat. The changed magnetic fields, as the patient rises, can be detected by feedback from the magnetic sensors, an analog-to-digital converter, and a micro-controller system which then can turn off the magnets.

Another operational requirement is driven by the fact that permanent magnets can lose strength due to various conditions that a permanent magnet finds itself exposed to over time. Technically, it is said that the remanent magnetization is demagnetized either partially or completely. External conditions that cause this demagnetization or loss of magnetic charge include external magnetic fields, physical shock and temperature fluctuations. Additionally, each permanent magnet can be demagnetized from magnetic fields internal to the magnet that are known as demagnetizing fields. Internal and external conditions may require that permanent magnets be re-magnetized or recharged over time. An electromagnet provides one method to recharge the permanent magnets in the body. The patient is removed from the wheelchair and placed face down on a bed. A straight-line electromagnet, placed directly above each permanent magnet in the body, is electrically pulsed to recharge each permanent magnet. The electric current direction of the pulse controls the magnetic polarity of the permanent magnet. Recharging the body permanent magnets can also be accomplished with multipole electromagnets, for example, a horseshoe magnet. The attractive force lifts the patient away from the bed and no pressure is applied to the skin of the lower pelvis.

The invention described here can be implemented with permanent magnets or equivalently with electromagnets below the seat of the wheelchair. The permanent magnet solution does not require continuous electric energy, while electromagnet solution requires fewer moving parts to implement. A permanent magnet embodiment and an electromagnet embodiment are described herein. In either embodiment, quadrupole repulsion is described between four permanent magnets in the pelvis and four magnets below the seat of a wheelchair. Higher pole configurations, such as six or eight poles, are possible.

Figure 2:
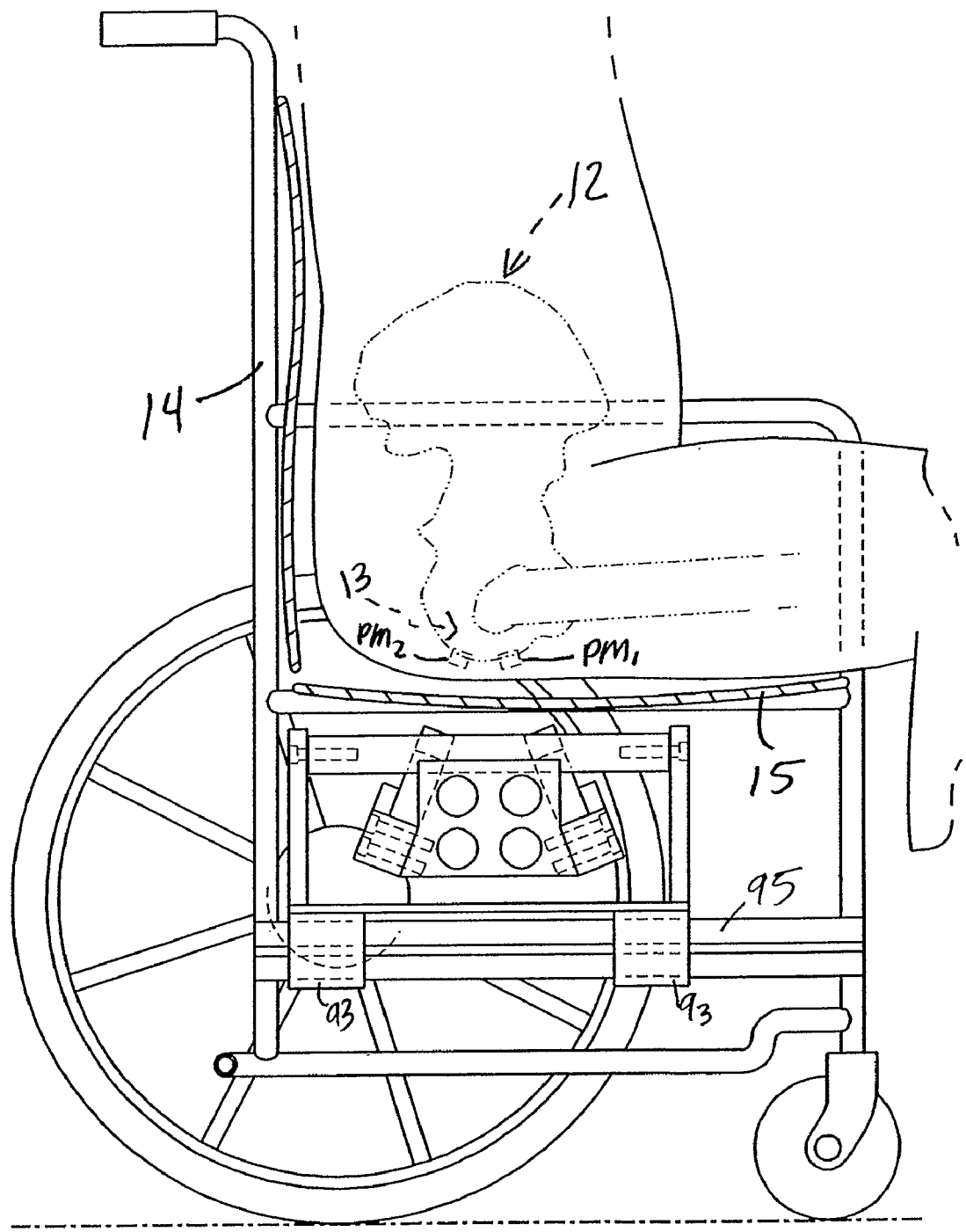
FIG. 2 is a partial side view of a wheelchair including an apparatus according to the invention for reducing compressive forces on soft tissue disposed between a human pelvis and the seat of the wheelchair.
Figure 4:
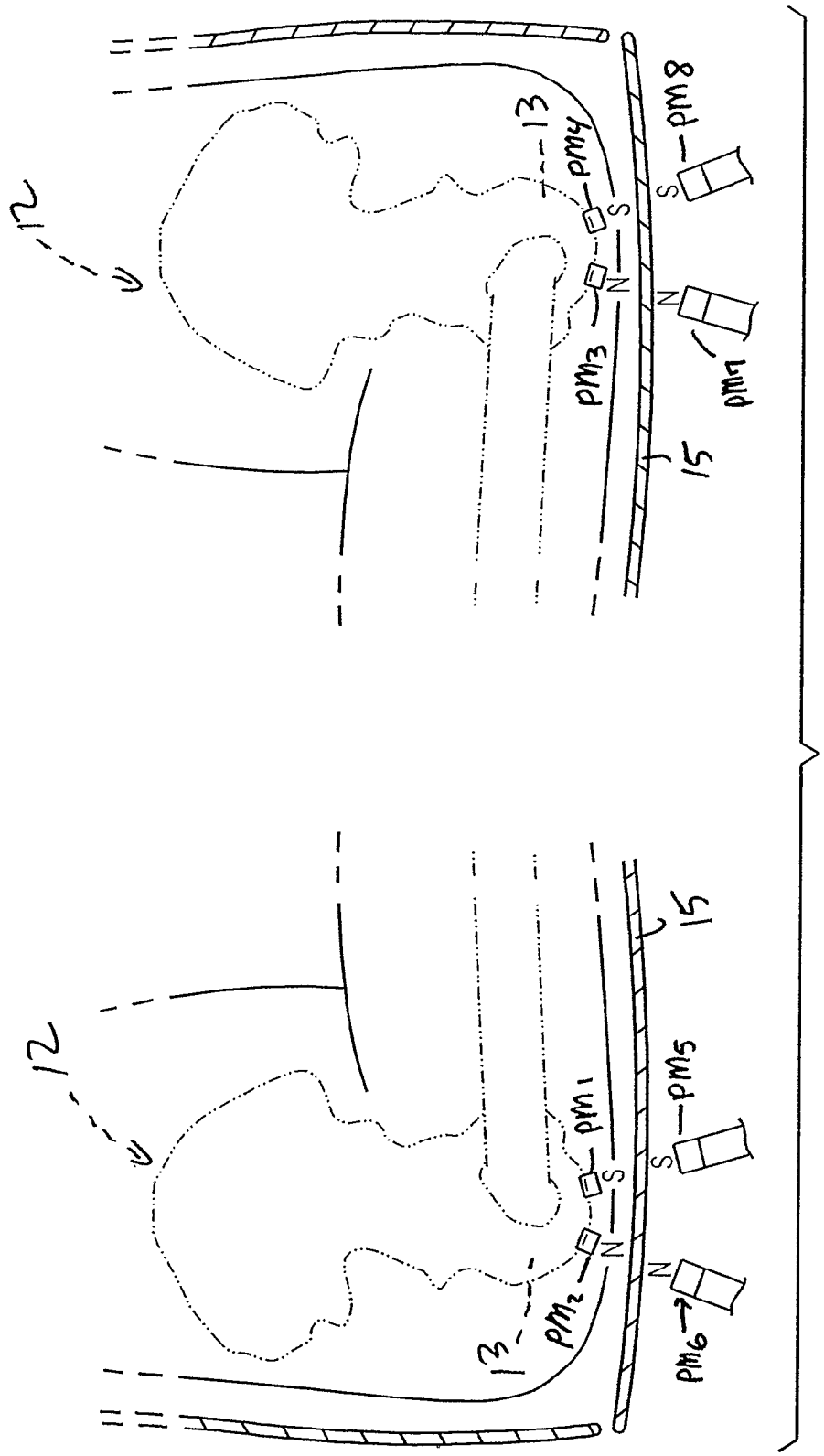
FIG. 4 shows right and left side views of pelvis magnets and magnets positioned below a wheel chair seat.

Referring now to FIG. 1, there is shown the right side of the human pelvis 12 which has the ischial tuberosity 13. The left side of the human pelvis 12, which also has the ischial tuberosity 13, is typically a mirror image of FIG. 1. The drawing at the right portion of FIG. 4 shows the left side of the pelvis 12. When in the seated position, the ischial tuberosities 13 are the lower-most points in the pelvis and it is at these two points that tissues are compressed the most due to the weight bearing down on a supporting structure such as a seat 15 of a wheelchair 14 (see FIG. 2).

Looking at FIGS. 1 and 4, permanent magnets $PM_1$ and $PM_2$ are secured robustly to the right ischial tuberosity 13 (osseointegration) through a surgical procedure. Likewise, permanent magnets $PM_3$ and $PM_4$ are secured robustly to the left ischial tuberosity 13. The permanent magnets $PM_1$, $PM_2$, $PM_3$, $PM_4$ may protrude slightly from the surface of the pelvis 12 or may not protrude from the surface of the pelvis 12. Surgical procedures have the capability to place the permanent magnets $PM_1$, $PM_2$, $PM_3$, $PM_4$ at the desired spacing in the lower human pelvis, and at the same time, control the orientation of these magnets. In the embodiment shown, four permanent magnets are placed within several centimeters of each other. Two permanent magnets $PM_2$ and $PM_4$ are placed on the posterior side of the ischial tuberosity 13 on each side of the body. Another two permanent magnets $PM_1$ and $PM_3$ are placed toward the pubic side or anterior to the ischial tuberosity 13 on each side of the body. The letters "N" and "S" indicate the poles of the magnets.

FIG. 4 shows the quadrupole permanent magnet embodiment below the wheelchair seat 15. The permanent magnets $PM_5$, $PM_6$, $PM_7$, $PM_8$ below the wheelchair seat 15 are one embodiment of how to lift the body with permanent magnets $PM_1$, $PM_2$, $PM_3$, $PM_4$ on or about the ischial tuberosity 13. FIGS. 3 and 4 show two right side permanent magnets $PM_5$ and $PM_6$ below the wheelchair seat 15 with a flux return path providing a low reluctance path between the permanent magnets $PM_5$ and $PM_6$. Magnetic flux flows from each pole piece of the four magnets in such a way that a repulsive force is set up between each magnet $PM_5$ and $PM_6$ below the wheelchair and with a corresponding permanent magnet $PM_1$ and $PM_2$ in the pelvis 12. This flux pattern creates a net force in the vertical direction and opposing forces in the horizontal direction.

A magnetic polarity configuration that gives lift and stability to the patient is chosen that matches the quadrupole polarity in the body to that below the wheelchair seat 15. Such a configuration is illustrated in FIG. 4. The four permanent magnets $PM_1$ and $PM_2$ and $PM_3$ and $PM_4$ in the body are acted on by the four magnets $PM_5$ and $PM_6$ and $PM_7$ and $PM_8$ below the wheelchair seat 15 to relieve skin pressure around the ischial tuberosity of the patient. The general purpose of the magnets below the wheelchair seat 15 is to partially levitate the patient. It is believed that a human weighing 68 kilograms, after partial levitation that produces an effective weight of 24 to 45 kilograms, will have sufficient blood flow in the areas of the buttocks to avoid sores.

Still looking at FIG. 4, the right side of the patient has north-north repulsion toward the posterior of the patient and south-south repulsion toward the anterior of the patient (see the left portion of FIG. 4). Conversely, the left side of the patient has south-south repulsion toward the posterior of the patient and north-north repulsion toward the anterior of the patient (see the right portion of FIG. 4). The preferred orientation of a body permanent magnet $PM_1$ and $PM_2$ and $PM_3$ and $PM_4$ with respect to its opposing permanent magnet $PM_5$, $PM_6$, $PM_7$, $PM_8$ below the wheelchair seat 15 is along the perpendicular bisector at the center of the pole piece of both opposing magnets. Such an orientation maintains stability under normal lift conditions while applying only axial forces to the body permanent magnets $PM_1$, $PM_2$, $PM_3$, $PM_4$ with no shear forces.

Figure 5:
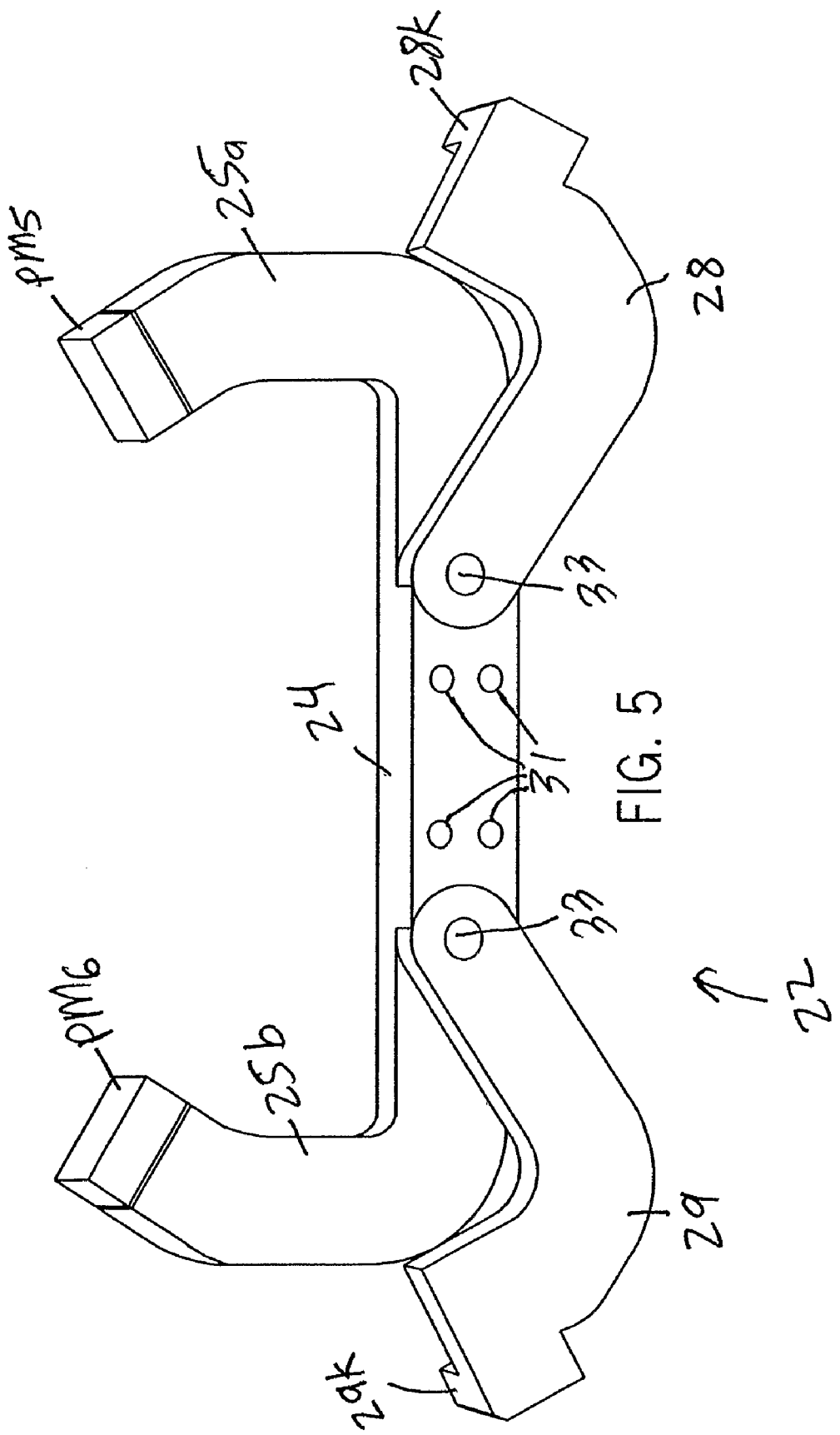
FIG. 5 shows a perspective view of a magnetic assembly of the invention in a normal lift position.

Referring to FIG. 5, there is shown a lower rear magnet assembly 22 of the invention. The lower rear magnet assembly 22 includes a central section 24 and permanent magnets $PM_5$, $PM_6$ and flux return paths 25a, 25b. The lower rear magnet assembly 22 also includes a variable reluctance arm 28 that terminates in a keeper 28k and a variable reluctance arm 29 that terminates in a keeper 29k. Mounting holes 31 are provided in the central section 24 of the lower rear magnet assembly 22, and the reluctance arms 28, 29 are pivotally mounted on the central section 24 of the lower rear magnet assembly 22 by pivot pins 33.

The patient under normal lift conditions is not at the maximum lift available from the permanent magnets. Some additional lift is reserved to transfer the patient out of the wheelchair (and with additional features, to shock-absorb the effects of the wheelchair's passage over uneven terrain). Variable lift is accomplished by changing the amount of flux that can flow through the return paths 25a, 25b; namely, the reluctance is varied in the return paths 25a, 25b between the two permanent magnets $PM_5$ and $PM_6$ of the lower magnet assembly 22. Such a flux return path with a variable reluctance path is shown in FIG. 5 under normal lift. Two moveable reluctance arms 28, 29 for each side of the flux return paths 25a, 25b are rotated out of the return path and reduce the magnet flux returned between the two permanent magnets $PM_5$ and $PM_6$ in the lower magnet assembly 22. Lift on the body from each permanent magnet is reduced because demagnetization fields internal to each permanent magnet are increased when the magnetic flux flow in the return path is limited.

Magnet materials for all permanent magnets $PM_5$ and $PM_6$ and the flux return paths 25a, 25b in the lower magnet assembly 22 is crucial to meet the operational requirements of a patient in a wheelchair 14. A soft magnetic material, such as cold-rolled steel, is needed to form the flux return paths 25a, 25b and the variable reluctance arms 28, 29 with associated keepers 28k, 29k. Suitable hard magnetic material candidates for the permanent magnets are NeFeB, SmCo, alnico and barium ferrite.

Figure 6:
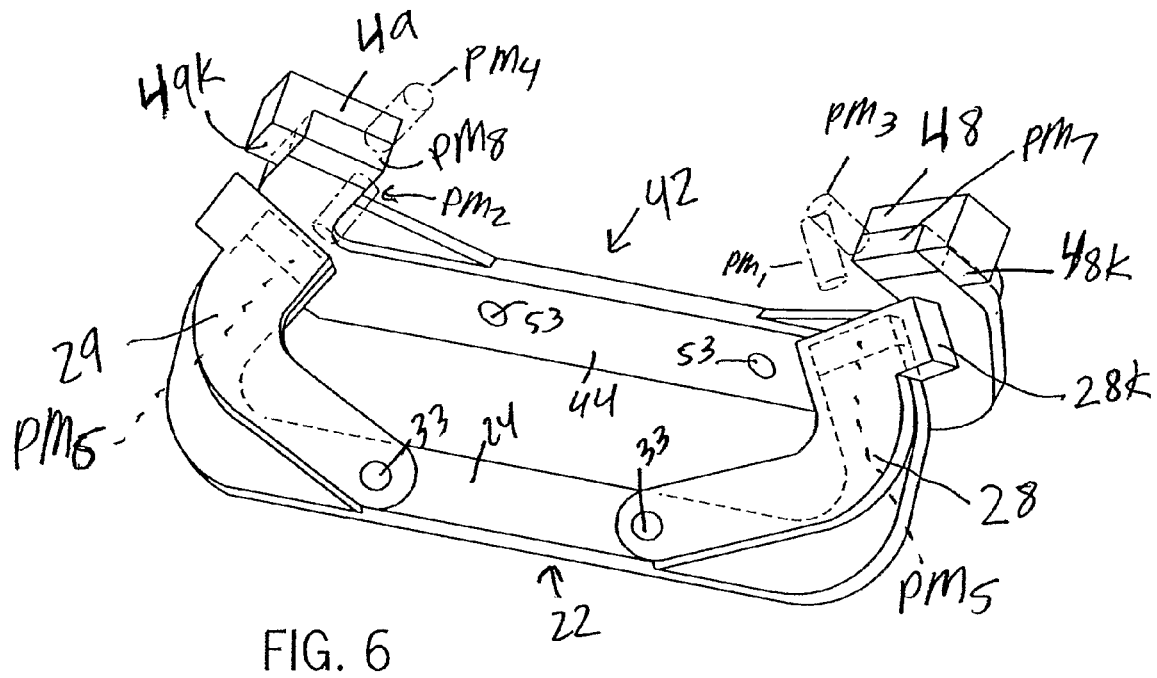
FIG. 6 shows a perspective view of two magnetic assemblies of the invention.

Looking at FIG. 6, a lower front magnet assembly 42 is shown which is similar in construction to the lower rear magnet assembly 22 and may use similar materials in all components. The lower front magnet assembly 42 includes a central section 44 and permanent magnets $PM_7$ $PM_8$ and flux return paths 45a, 45b. The lower front magnet assembly 42 also includes a variable reluctance arm 48 that terminates in a keeper 48k and a variable reluctance arm 49 that terminates in a keeper 49k. Mounting holes 51 are provided in the central section 44 of the lower front magnet assembly 42, and the reluctance arms 48, 49 are pivotally mounted on the central section 44 of the lower right magnet assembly 42 by pivot pins 53.

Still looking at FIG. 6, both lower magnet assemblies 22, 42 are placed in juxtaposition to the body permanent magnets $PM_1$, $PM_2$, $PM_3$, $PM_4$ as seen in an isometric view in FIG. 6 to provide an overall view of how the magnet forces are applied to the patient. The magnet assemblies in aggregate apply a net vertical force to the body permanent magnets $PM_1$, $PM_2$, $PM_3$, $PM_4$ and apply no net lateral forces to the body permanent magnets $PM_1$, $PM_2$, $PM_3$, $PM_4$ in equilibrium. Net vertical force causes the magnetic lift required for skin blood flow in the lower pelvis. Lateral forces are necessary for the stability of the patient. At equilibrium, there are no net horizontal forces but patient lateral movement, anterior-to-posterior or right-to-left, causes the body permanent magnets $PM_1$, $PM_2$, $PM_3$, $PM_4$ to see restore forces to equilibrium. If a patient moves right to left, equilibrium is restored by the lower assembly permanent magnets $PM_6$, $PM_8$ on the left side of the patient applying more lateral force on the left body permanent magnets to the right while the lower assembly magnets $PM_5$ and $PM_7$ on the right side apply less force on the right body permanent magnets to the left. Restoring forces create stability against lateral patient movements that are left-to-right, and anterior-to-posterior. Orientation of the two lower magnet assemblies 22, 42 is left-to-right in FIG. 6, but the orientation of the two lower magnet assemblies 22, 42 can equally be anterior-to-posterior as in FIGS. 3 and 4.

Figure 7:
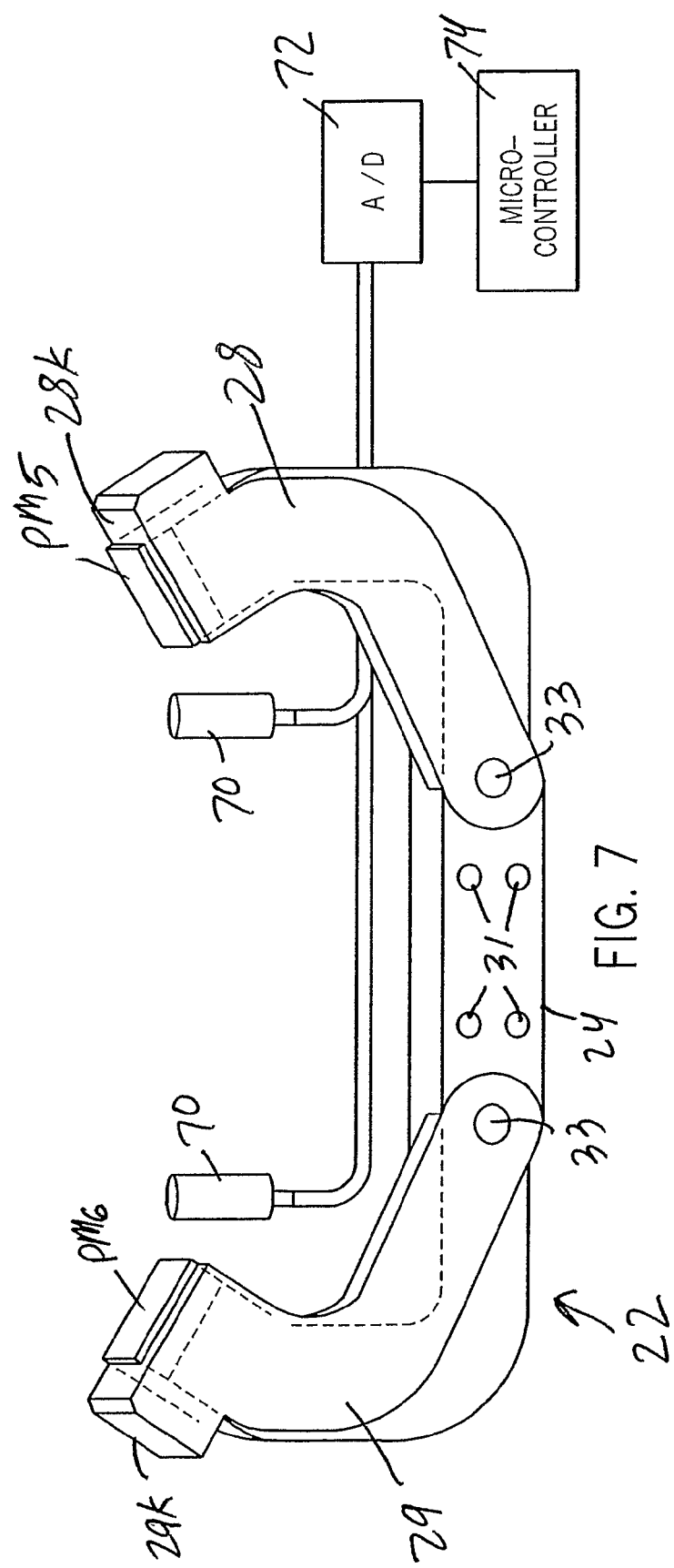
FIG. 7 shows a perspective view of the magnetic assembly of FIG. 5 in a shunting position.

Referring to FIG. 7, patient transfer into a wheelchair requires that magnets below the seat be off in order to prevent the patient from experiencing magnetic attraction if the patient lands at the wrong position in the seat. Patient protection in the permanent magnet embodiment below the wheelchair seat 15 is accomplished by magnetically shorting the permanent magnets $PM_5$, $PM_6$, $PM_7$, $PM_8$ below the seat 15 with keepers 28k, 29k, 48k, 49k. FIG. 7 shows the keeper sections 28k, 29k at the ends of variable reluctance arms 28, 29 shunting, or shorting, so that the body permanent magnets $PM_5$ and $PM_6$ feel no force from the magnetic flux of the lower rear magnet assembly 22. The keepers 28k, 29k, placed about the upper pole pieces $PM_5$ and $PM_6$ of the lower magnet assembly 22, shunt the magnetic flux away from the body permanent magnets back onto the lower assembly permanent magnets $PM_5$ and $PM_6$ themselves. To verify that the permanent magnets in the body are aligned with the lower magnet assemblies in repulsion, magnetic field sensors 70 are placed about the lower assembly pole pieces. The variable reluctance arms 28, 29 are allowed to drop to their normal operating position to turn lift on, but only after the magnet sensors detect alignment of the body to the lower assembly permanent magnets $PM_1$, $PM_2$. The lower front magnet assembly 42 works in the same manner as the lower rear magnet assembly 22.

Looking at FIG. 8, patient transfer out of a wheelchair places three requirements on the lower magnet assemblies 22, 42: a patient and caregiver requirement that relieves upper body stress during the initial part of the transfer, a safety requirement that the lift of the lower permanent magnets $PM_5$, $PM_6$, $PM_7$, $PM_8$ be turned off as the patient rise out of the wheelchair, and another safety requirement that the lower magnet lift be kept off in preparation for the patient's eventual return to the wheelchair 14. Additional lift is used for relieving upper body stress on the patient or caregiver during transfer of the patient out of the wheelchair. FIG. 8 illustrates how the additional boost is created by moving the variable reluctance arms 28, 29 to a position of lowest reluctance which maximizes flux flow along the return path 25a, 25b. Lift on the body from each permanent magnet $PM_5$ and $PM_6$ is increased because demagnetization fields internal to each permanent magnet $PM_5$ and $PM_6$ are decreased when the magnetic flux flow in the return paths 25a, 25b is maximized. A transient boost to lift on the body takes place as the reluctance arms 28, 29 move from their normal lift position to its maximum lift position. Upper body stress is reduced if the patient transition out of the wheelchair takes place during and after the variable reluctance arms 28, 29 are moved into the maximum lift position.

Safety considerations, namely, preventing the patient's body from ever being under an attractive magnet force, requires that the keepers 28k, 29k on the variable reluctance arms 28, 29 shunt out the lower magnet assembly permanent magnets $PM_5$ and $PM_6$ (see FIG. 7) on a timely basis. The lower magnet assembly pole pieces are shunted as magnetic sensors 70 determine that the patient's initial departure from the wheelchair has begun and before the patient could possibly fall back into the wheelchair. Alignment of the body to the proper magnetic poles is sensed by the magnetic field sensors 70 and connected to the usual electronic configuration of an analog-to-digital converter 72 that is input to a digital micro-controller 74 (see FIG. 8). The micro-controller 74 then provides positional feedback to humans or a mechanical compensation system for the body position. After successful transfer out of the wheelchair, the lower magnet assembly pole pieces are to remain shunted in preparation for the patient's transfer back into the wheelchair.

Figure 9:
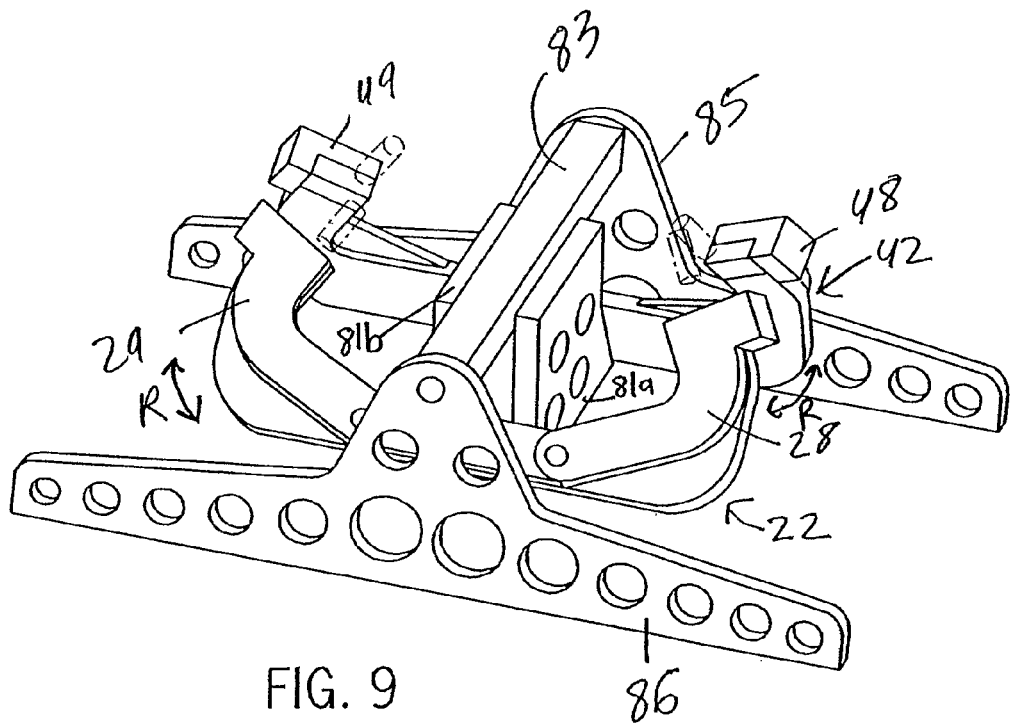
FIG. 9 shows a perspective view of two magnetic assemblies of the invention assembled on end brackets for rotation.

Referring to FIG. 9, load shifting of the body from side to side can be accomplished by simultaneous mechanical rotation of both lower magnet assemblies 22,42. The lower magnet assemblies 22,42 are mounted to brackets 81a, 81b that are mounted to a horizontal pivot bar 83. The horizontal pivot bar 83 is journaled for rotation between a front transverse bracket 85 and a rear transverse bracket 86. The right-to-left orientation of the flux return path is shown for the lower magnet assemblies 22, 42. Rotation (in directions R) of lower magnetic assemblies 22, 42 produces more force on one side of the body than the other side of the body which brings about load shift. Rotation of the horizontal pivot bar 83 can be achieved by a suitable coupling from the horizontal pivot bar 83 to a conventional motor under suitable electronic control (e.g., digital micro-controller 74).

Variation of force from one side of the body to the other side of the body can also be produced by moving the variable reluctance arms 28, 29, 48, 49. Rotation of the variable reluctance arms 28, 29, 48, 49 can be achieved by a suitable coupling from the arms 28, 29, 48, 49 to conventional motor under suitable electronic control. The variable reluctance arms on one side of the body are moved toward the maximum lift position (FIG. 8) while keeping both variable reluctance arms on the other side of the body in the normal lift position (FIG. 5). In the right-to-left orientation of the flux return path, the arms moved toward the maximum lift position are on different lower magnet assemblies. Load shifting by reluctance changes, while causing rotation of the patient's body, requires no mechanical rotation of the lower assembly. Load shifting by reluctance changes can be used with or without the assistance from mechanical rotation of the lower assemblies on the horizontal pivot bar 83.

Load shifting can also be implemented for lower magnet assemblies with an anterior-to-posterior orientation of the flux return path. Mechanical rotation only requires that the brackets 85, 86, connecting the pivot bar 83 in FIG. 9 and the two lower assemblies 22, 42, be rotated by ninety degrees. Load shifting by variable reluctance in an anterior-to-posterior orientation of the return path means that both arms, which are moved toward the maximum lift position, are on the same flux return path.

Figure 10:
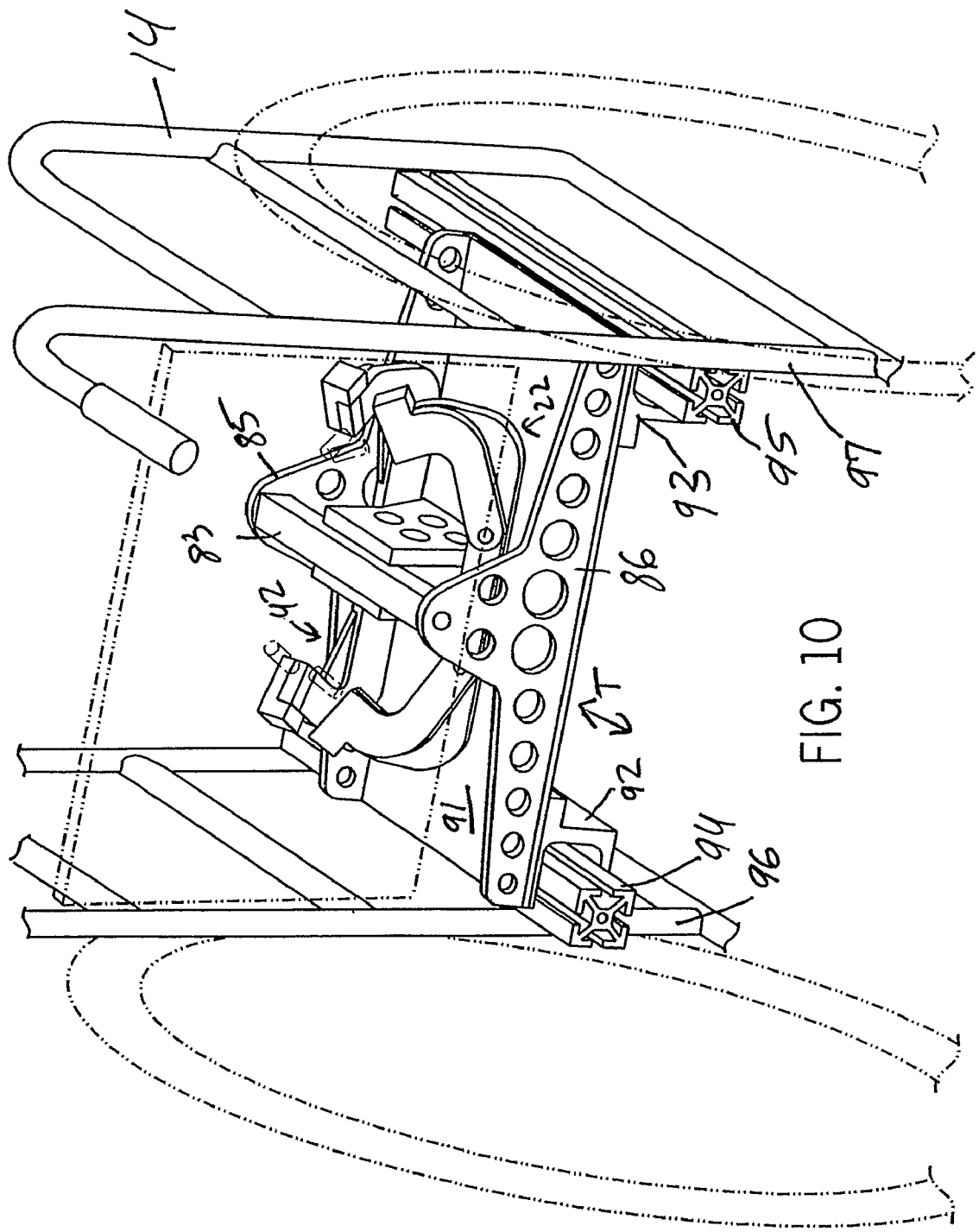
FIG. 10 shows a wheelchair including an apparatus according to the invention.

Referring now to FIG. 10, magnet alignment between the body permanent magnets $PM_1$, $PM_2$, $PM_3$, $PM_4$ and the lower magnet assemblies 22, 42 requires that the both of the lower magnet assemblies 22, 42 can be moved either anteriorly or posteriorly. Such a magnet alignment is needed to accommodate various body postures in the wheelchair seat 15 and to accommodate various body positions after transfer into the wheelchair 14. The configuration in FIG. 10 allows for anterior/posterior movement of both lower magnet assemblies and the load shift mechanism as a complete unit. Specifically, the front transverse bracket 85 and the rear transverse bracket 86 are mounted on a base plate 91. The base plate 91 has a pair of lower left spaced apart C-shaped brackets 92 and a pair of right spaced apart C-shaped brackets 93 (see also FIG. 2). The wheelchair 14 has a left slide bar 94 and a right slide bar 95 that are mounted to wheel chair supports 96, 97 respectively. The base plate 91 is assembled to the wheelchair 14 by placing the left slide bar 94 in the left spaced apart C-shaped brackets 92 and by placing the right slide bar 95 in the right spaced apart C-shaped brackets 93. The base plate 91 can then translate in front and rear directions T on the left slide bar 94 and right slide bar 95 to provide anterior/posterior movement of both lower magnet assemblies and the load shift mechanism as a complete unit. Translation of the base plate 91 can be achieved by a suitable coupling from the base plate 91 to a conventional motor under suitable electronic control.

Figure 11:
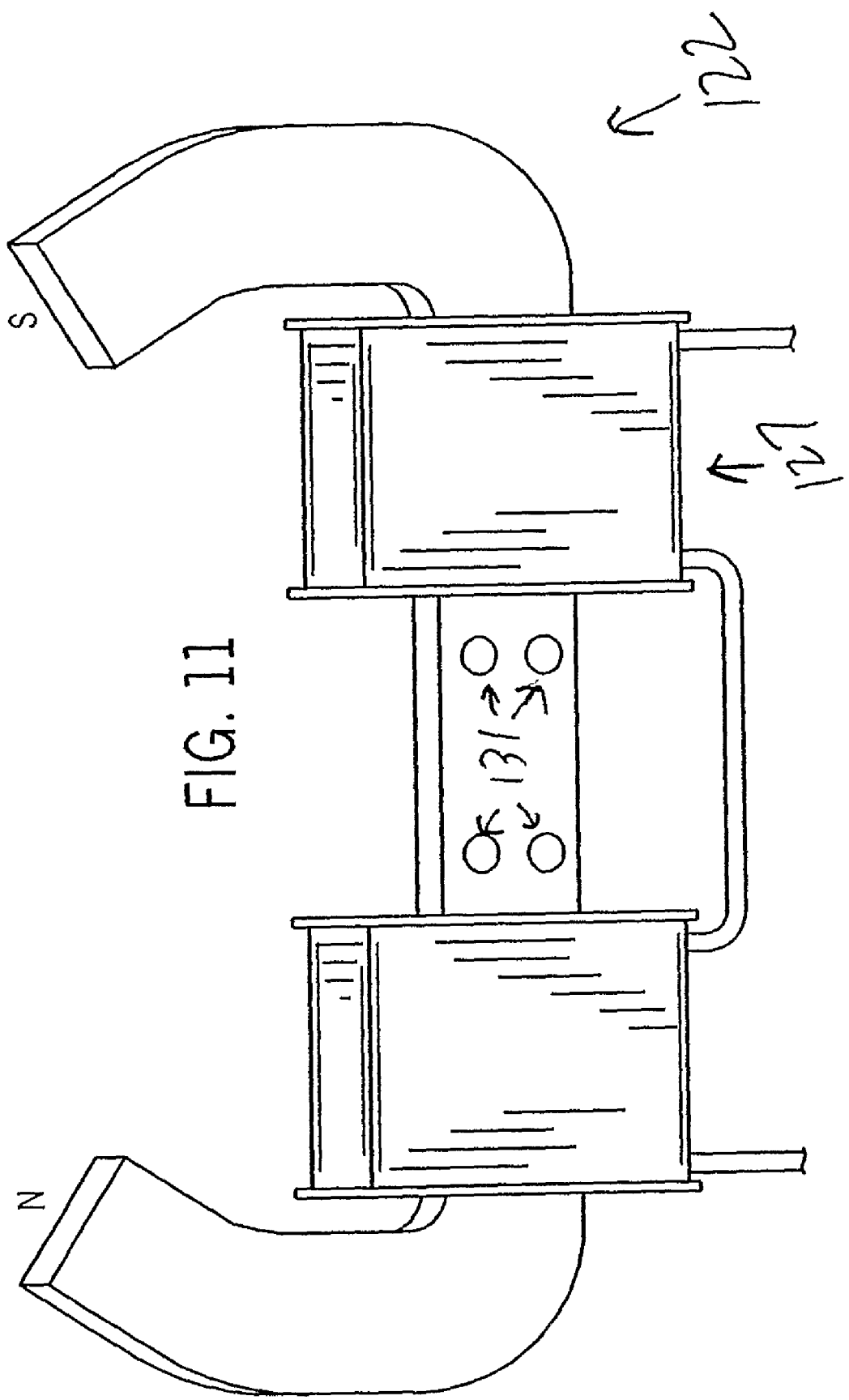
FIG. 11 shows a perspective view of an electromagnetic assembly for use in the invention.

Looking at FIG. 11, there is shown a lower electromagnetic assembly 122 for use in a quadrupole electromagnet embodiment of the invention. Electromagnets can equivalently be implemented below the wheelchair seat 15 as can the lower magnet assemblies 22, 42 using permanent magnets $PM_5$, $PM_6$, $PM_7$, $PM_8$. Lift conditions required for normal lift, patient transfer into the wheelchair, and patient transfer out of the wheelchair is accomplished by electrical current control. Load shifting using only current control is an option without permanent magnets below the wheelchair seat. Electromagnet and permanent magnet implementations below the wheelchair seat 15 have the same magnetic flux repulsion pattern with body magnets as in FIG. 3; the only difference is the permanent magnet is removed and flux comes directly from the soft magnetic flux path. A lower electromagnet 122 consists of a soft magnetic material with a wound wire coil 127 to drive the magnetic field as shown in FIG. 11. The coil is broken into two sections to make clearance for the connecting bracket mounting holes 131. In contrast to FIG. 5, there are no permanent magnets nor variable reluctance arms. As the permanent magnet embodiment below the wheelchair has two assemblies in FIG. 6, the electromagnet embodiment likewise can include two electromagnets 122. Similarly, the orientation of the electromagnets 122 is either posterior-to-anterior or right-to-left as in the permanent magnet embodiment of FIGS. 2-10.

The three modes of wheelchair operation, normal lift, transfer of the patient into the wheelchair, and transfer out of the wheelchair, are implemented by electric current control using electromagnetic assemblies 122 without any moving parts. Just as in the permanent magnet embodiment, normal lift is not a maximum but some lift is reserved for transfer out of the wheelchair. The electromagnet embodiment has a net vertical force and zero lateral force in equilibrium as is the case of the permanent magnet embodiment. Likewise, patient transfer into the wheelchair is done under little or no lift which requires that the electromagnet coils have no current in them and, possibly, be demagnetized before the transfer process. Demagnetization of the flux return path, if needed, is implemented by an alternating current (AC) decaying in time (a.k.a. AC demagnetization) or by a current pulse reaching the magnet's coercivity remanence point and then turning off. As in the permanent magnet case, the electromagnets are energized to normal lift after the magnet sensors about the electromagnet pole faces sense the correct polarity of body magnets from the patient. Transfer out of a wheelchair by a patient or caregiver can be assisted by the patient. Transfer out of a wheelchair by a patient or caregiver can be assisted by more lift than normal lift. Lift is increased by running the electromagnets into magnetic saturation using additional current through the coils than during normal operation. Magnetic lift from the electromagnets below the wheelchair must be turned off to protect the patient during a fall back into the wheelchair immediately after the initial patient departure from the chair as in the permanent magnet case. Magnetic sensors close to the electromagnet pole pieces are used to sense the patient's departure from the chair. Lift is turned off by stopping current to the electromagnet coils and demagnetizing the electromagnets if needed. Each electromagnet remains without current excitation until the patient returns to the wheelchair and the sensors determine proper positioning of the patient.

Side-to-side load shift, under anterior-to-posterior electromagnet orientation, is accomplished by increasing electric current on one side of the body and decreasing current on the other side of the body. Variation of lift from side to side is compatible with mechanical rotation as in FIG. 9. Mechanical rotation can assist electric current rotation or not as needed. The base slide mechanism is the same for the permanent magnet and electromagnet embodiments. Patient anterior-to-posterior adjustment to align with body magnets after transfer into the wheelchair and patient posture variation needs to be accommodated in either the permanent magnet or electromagnet implementation below the wheelchair seat.

While both the permanent magnet embodiment and the electromagnet embodiment below the wheelchair seat are described above as separate embodiments, permanent magnets and electromagnets below the wheelchair seat are not mutually exclusive and can be used together as needed. For instance, an electromagnet could boost lift in the permanent magnet embodiment below the wheelchair seat. Likewise, a permanent magnet could boost lift in the electromagnet embodiment below the wheelchair seat. In the embodiment in which the permanent magnets provide the primary lift and the electromagnets provide the secondary lift, or when the electromagnets provide all of the lift, a closed-loop microprocessor-mediated (or microcontroller-mediated) feedback control mechanism can be established by employing the magnetic sensors 70 under the wheelchair seat (as described above) in conjunction with appropriately written software in microcontroller 74 to implement several of the features described above. One example of this computer-mediated behavior of the chair is the ability to shift the patient from side to side automatically by increasing the electromagnet-generated magnetic forces on one side of the patient while decreasing the electromagnet-generated magnetic forces on the other side of the patient, and then vice versa. The computerized system could alternate the patient's weight-bearing posture on a timed interval basis in this manner, and also assist in the removal of the patient from the chair or return to the chair. An additional use of the computer-controlled sensor-actuator feedback loop would be a shock absorption function if the wheelchair traverses uneven terrain; the electromagnet portion of the system could supply additional lift for a short duration to counteract downward forces caused by rough terrain to keep the patient at a constant height above the wheelchair seat.

The wheelchair seat 15 can be integrated onto the pole pieces below the wheelchair seat 15 in both the permanent magnet embodiment and the electromagnet embodiment. Such a custom seat offers patient safety, maximum lift, and patient comfort. Maximum lift on the patient is set because the thickness of the seat determines a minimum spacing between the body magnets and the lower magnets. If polarity between the body magnets and the lower magnets becomes attractive, patient safety is protected because the seat thickness sets a maximum attractive force. Finally, the comfort of the patient can be aided by the shape of the seat formed on each pole piece.

Figure 12:
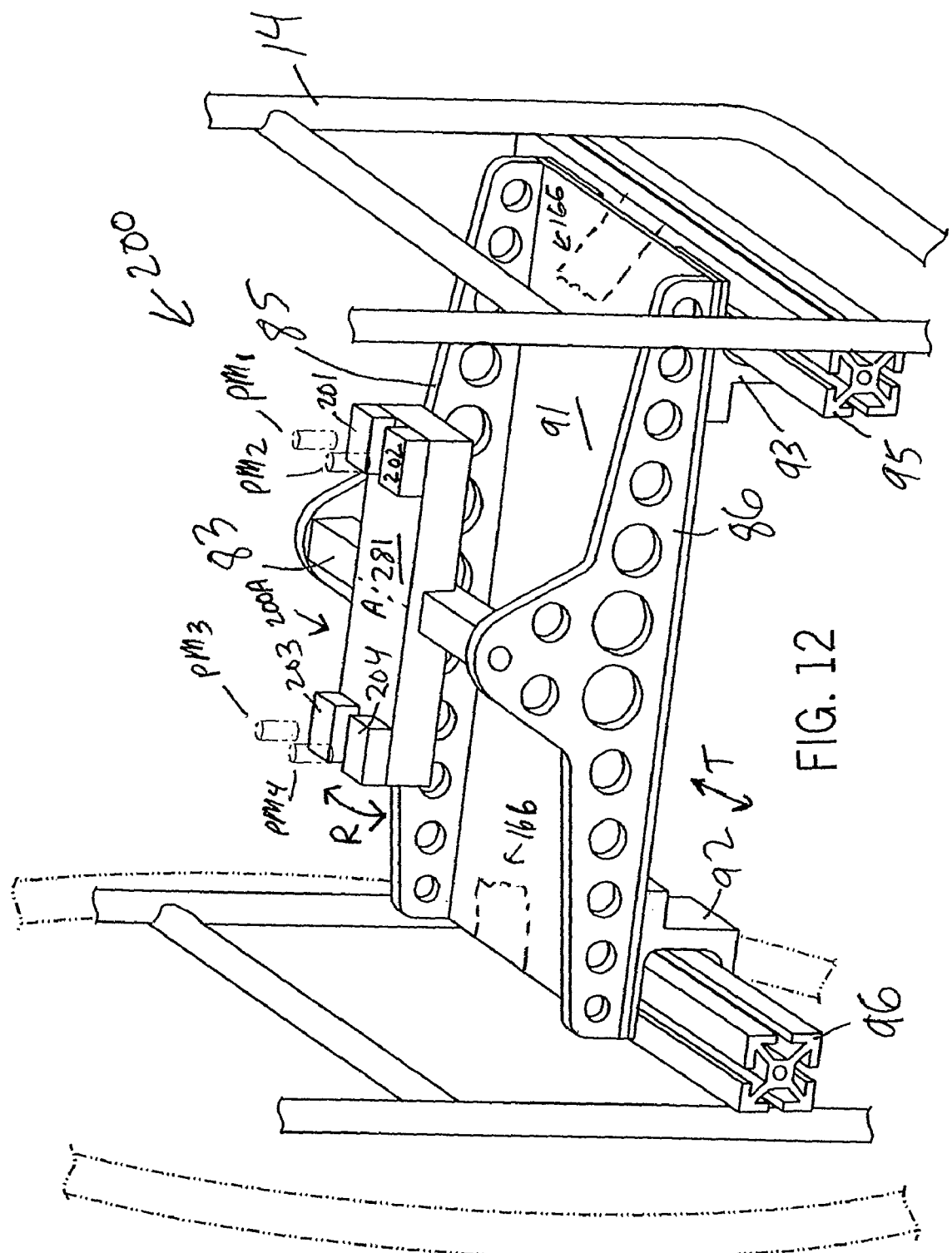
FIG. 12 shows a wheelchair including another apparatus according to the invention.

Looking at FIG. 12, there is shown a unipolar apparatus 200 of the invention on the wheelchair 14 that uses mechanical restraints for patient stability. The apparatus 200 includes the front transverse bracket 85 and the rear transverse bracket 86 mounted on the base plate 91 as in FIG. 10. The base plate 91 has the C-shaped brackets 92, 93 as in FIG. 10. The wheelchair 14 has the slide bars 94, 95 as in FIG. 10. The base plate 91 can translate in front and rear directions T on the slide bars 94,95 to provide anterior/posterior movement of a unipolar magnetic assembly 200A by a suitable coupling from the base plate 91 to a conventional motor under suitable electronic control. The unipolar magnetic assembly 200A includes four permanent magnets 201, 202, 203, 204 mounted at the four corners of a rectangular mounting base 281 that is mounted on the rotating horizontal pivot bar 83 for rotation in directions R about axis A of the base 281. In the embodiment of FIG. 12, the north pole of each permanent magnet 201, 202, 203, 204 faces up and the north pole of each of the body permanent magnets $PM_1$, $PM_2$, $PM_3$, $PM_4$ faces down. The four body permanent magnets $PM_1$ and $PM_2$ and $PM_3$ and $PM_4$ in the body are acted on by the four magnets 201, 202, 203, 204 below the wheelchair seat 15 to relieve skin pressure around the ischial tuberosity of the patient.

Patient stability under partial magnet levitation or lift is mechanically implemented by a restraint belt 166 (shown in partial view and in dashed lines) about the belly or chest. Additional stability is available by securing the patient's feet and shoes in the foot pedals of the wheelchair, if needed. A unipolar magnetic lift as in FIG. 12 is used since no stability requirements are made of the magnet system. Furthermore, the lift is completely vertical with no lateral magnet forces needed for patient stabilization. Magnet pole piece orientation below the wheelchair is horizontal which allows for larger pole pieces that area closer to the body magnets. More lift is available to the patient because the lower magnet pole pieces are larger and because they are closer to the body magnets. Unipolar lift has no possibility of the patient experiencing attractive magnet forces due to unintended patient positioning within the wheelchair. Lift can be accomplished using permanent magnets, electromagnets, or a combination of both, either with or without sensor-mediated computerized feedback control (as described above). Additional patient stability is available from asymmetric-sized pole pieces by making the anterior pole pieces larger than the posterior pole pieces. Asymmetric anterior-to-posterior lift creates a rotational force that pushes the patient's upper body into the back of the wheelchair.

The unipolar embodiment of FIG. 12 is implemented in the wheelchair in a similar way to the permanent magnet and electromagnet quadrupole embodiments above. Magnetic forces do not need to be turned off during transfer of the patient into or out of the wheelchair. Magnetic field sensing to determine body magnet alignment to the lower pole pieces is not needed to avoid patient attraction but it is still useful for patient locating in the seat. Side-to-side load shifting can be implemented mechanically or magnetically as in the permanent magnet and electromagnet multipole embodiments described above. Base plate 91 slide motion is implemented as was discussed above in the permanent magnet and electromagnet multipole embodiments.

Therefore, it can be seen that the invention provides an apparatus and method for reducing compressive forces on soft tissue disposed between a bone, such as a human pelvis, and a supporting structure, such as the seat of a wheel chair.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

INDUSTRIAL APPLICABILITY

The invention provides an apparatus and method for reducing compressive forces on soft tissue disposed between a bone and a supporting structure, thereby reducing the tendency for decubitus ulceration.

What is claimed is:

1. An apparatus for reducing compressive forces on soft tissue disposed between a bone in a subject and a supporting structure, the apparatus comprising:
    a first bone magnet suitable for implantation into the bone;
    a second bone magnet suitable for implantation into the bone;
    a first support structure magnet attached to a base positioned adjacent the supporting structure;
    a second support structure magnet attached to the base, and
    means for moving the base with respect to the supporting structure,
    wherein the first bone magnet and the first support structure magnet are positioned such that a repelling force is produced that acts on the first bone magnet and the first support structure magnet to reduce the compressive force acting on the soft tissues disposed therebetween, and
    wherein the second bone magnet and the second support structure magnet are arranged such that a repelling force is produced that acts on the second bone magnet and the second support structure magnet to reduce the compressive force acting on the soft tissues disposed therebetween.

2. The apparatus of claim 1 wherein the means for moving the base comprises:
    means for rotating the base about an axis of the base such that the first bone magnet can move away or toward the first support structure magnet and such that the second bone magnet can move away or toward the second support structure magnet.

3. The apparatus of claim 1 wherein the means for moving the base comprises:
    means for translating the base such that the first bone magnet can move away or toward the first support structure magnet and such that the second bone magnet can move away or toward the second support structure magnet.

4. The apparatus of claim 1 wherein:
    the first support structure magnet and the second support structure magnet are spaced apart on opposite sides of an axis of the base.

5. The apparatus of claim 1 wherein:
    the supporting structure is a seat of a wheelchair, and the bone is a human pelvis.

6. The apparatus of claim 1 further comprising:
    a third bone magnet suitable for implantation into the bone;
    a fourth bone magnet suitable for implantation into the bone;
    a third support structure magnet attached to the base;
    a fourth support structure magnet attached to the base;
    wherein the third bone magnet and the third support structure magnet are positioned such that a repelling force is produced that acts on the third bone magnet and the third support structure magnet to reduce the compressive force acting on the soft tissues disposed therebetween, and wherein the fourth bone magnet and the fourth support structure magnet are arranged such that a repelling force is produced that acts on the fourth bone magnet and the fourth support structure magnet to reduce the compressive force acting on the soft tissues disposed therebetween.

7. The apparatus of claim 6 wherein:
the first support structure magnet and the second support structure magnet are positioned in spaced relationship on a side of an axis of the base, and
the third support structure magnet and the fourth support structure magnet are positioned in spaced relationship on an opposite side of the axis of the base.

8. The apparatus of claim 7 wherein:
the first support structure magnet has a larger pole piece than the second support structure magnet, and
the third support structure magnet has a larger pole piece than the fourth support structure.

9. The apparatus of claim 1 wherein:
the first support structure magnet and the second support structure magnet are electromagnets.

10. The apparatus of claim 1 wherein:
the first support structure magnet and the second support structure magnet are permanent magnets.

11. The apparatus of claim 1 wherein:
the supporting structure is a seat of a wheelchair, and
the wheelchair includes a mechanical restraint.

12. The apparatus of claim 1 wherein:
the first support structure magnet and the second support structure magnet are spaced apart on opposite sides of an axis of the base, and
the apparatus further comprises means for increasing and decreasing magnetic flux flow in the first support structure magnet and the second support structure magnet.

13. The apparatus of claim 1 wherein:
the first support structure magnet and the second support structure magnet are positioned below the supporting structure.

14. An apparatus for reducing compressive forces on soft tissue disposed between a bone in a subject and a supporting structure, the apparatus comprising:
a first bone magnet suitable for implantation into the bone;
a second bone magnet suitable for implantation into the bone;
a first support structure magnet positioned adjacent the supporting structure;
a second support structure magnet positioned adjacent the supporting structure,
means for increasing and decreasing magnetic flux flow in the first support structure magnet and the second support structure magnet;
wherein the first bone magnet and the first support structure magnet are positioned such that a first repelling force from north-north magnetic repulsion is produced that acts on the first bone magnet and the first support structure magnet to reduce the compressive force acting on the soft tissues disposed therebetween, and
wherein the second bone magnet and the second support structure magnet are arranged such that a second repelling force from south-south magnetic repulsion is produced that acts on the second bone magnet and the second support structure magnet to reduce the compressive force acting on the soft tissues disposed therebetween.

15. The apparatus of claim 14 further comprising:
means for moving a base with respect to the supporting structure, wherein the first support structure and the second support structure are attached to the base.

16. The apparatus of claim 15 wherein the means for moving the base comprises:
means for rotating the base about an axis of the base such that the first bone magnet can move away or toward the first support structure magnet and such that the second bone magnet can move away or toward the second support structure magnet.

17. The apparatus of claim 15 wherein the means for moving the base comprises:
means for translating the base such that the first bone magnet can move away or toward the first support structure magnet and such that the second bone magnet can move away or toward the second support structure magnet.

18. The apparatus of claim 15 wherein:
the first support structure magnet and the second support structure magnet are spaced apart on opposite sides of an axis of the base.

19. The apparatus of claim 14 wherein:
the supporting structure is a seat of a wheelchair, and
the bone is a human pelvis.

20. The apparatus of claim 14 further comprising:
a third bone magnet suitable for implantation into the bone;
a fourth bone magnet suitable for implantation into the bone;
a third support structure magnet positioned adjacent the supporting structure;
a fourth support structure magnet positioned adjacent the supporting structure,
wherein the third bone magnet and the third support structure magnet are positioned such that a third repelling force from north-north magnetic repulsion is produced that acts on the third bone magnet and the third support structure magnet to reduce the compressive force acting on the soft tissues disposed therebetween, and
wherein the fourth bone magnet and the fourth support structure magnet are arranged such that a fourth repelling force from south-south magnetic repulsion is produced that acts on the fourth bone magnet and the fourth support structure magnet to reduce the compressive force acting on the soft tissues disposed therebetween.

21. The apparatus of claim 20 wherein:
the first support structure magnet and the second support structure magnet are positioned in spaced relationship on a side of an axis of a base, and
the third support structure magnet and the fourth support structure magnet are positioned in spaced relationship on an opposite side of the axis of the base, and
the apparatus further comprises means for moving the base with respect to the supporting structure.

22. The apparatus of claim 14 wherein:
the first support structure magnet and the second support structure magnet are electromagnets.

23. The apparatus of claim 14 wherein:
the first support structure magnet and the second support structure magnet are permanent magnets.

24. The apparatus of claim 14 wherein:
the first support structure magnet and the second support structure magnet are positioned below the supporting structure.

25. An apparatus for reducing compressive forces on soft tissue disposed between a bone in a subject and a supporting structure, the apparatus comprising:

a first bone magnet suitable for implantation into the bone;
a second bone magnet suitable for implantation into the bone;
a first support structure magnet positioned adjacent the supporting structure;
a second support structure magnet positioned adjacent the supporting structure,
means for sensing alignment of the first bone magnet and the first support structure magnet;
wherein the first bone magnet and the first support structure magnet are positioned such that a first repelling force from north-north magnetic repulsion is produced that acts on the first bone magnet and the first support structure magnet to reduce the compressive force acting on the soft tissues disposed therebetween, and
wherein the second bone magnet and the second support structure magnet are arranged such that a second repelling force from south-south magnetic repulsion is produced that acts on the second bone magnet and the second support structure magnet to reduce the compressive force acting on the soft tissues disposed therebetween.

26. The apparatus of claim 25 further comprising:
means for moving a base with respect to the supporting structure, wherein the first support structure and the second support structure are attached to the base.

27. The apparatus of claim 25 wherein:
the supporting structure is a seat of a wheelchair, and
the bone is a human pelvis.

28. The apparatus of claim 25 further comprising:
a third bone magnet suitable for implantation into the bone;
a fourth bone magnet suitable for implantation into the bone;
a third support structure magnet positioned adjacent the supporting structure;
a fourth support structure magnet positioned adjacent the supporting structure,
wherein the third bone magnet and the third support structure magnet are positioned such that a third repelling force from north-north magnetic repulsion is produced that acts on the third bone magnet and the third support structure magnet to reduce the compressive force acting on the soft tissues disposed therebetween, and
wherein the fourth bone magnet and the fourth support structure magnet are arranged such that a fourth repelling force from south-south magnetic repulsion is produced that acts on the fourth bone magnet and the fourth support structure magnet to reduce the compressive force acting on the soft tissues disposed therebetween.

29. The apparatus of claim 25 wherein:
the first support structure magnet and the second support structure magnet are electromagnets.

30. The apparatus of claim 25 wherein:
the first support structure magnet and the second support structure magnet are permanent magnets.

* * * * *